(12) United States Patent
Suzuki et al.

(10) Patent No.: US 11,154,184 B2
(45) Date of Patent: Oct. 26, 2021

(54) CONTROL APPARATUS FOR ENDOSCOPE APPARATUS AND ENDOSCOPE APPARATUS

(71) Applicant: OLYMPUS CORPORATION, Tokyo (JP)

(72) Inventors: Takashi Suzuki, Hino (JP); Yoshitaka Umemoto, Hachioji (JP); Yasuaki Natori, Akishima (JP); Takashi Yamashita, Hachioji (JP); Fumiyuki Onoda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 304 days.

(21) Appl. No.: 16/411,310

(22) Filed: May 14, 2019

(65) Prior Publication Data

US 2019/0261832 A1 Aug. 29, 2019

Related U.S. Application Data

(63) Continuation of application No. PCT/JP2017/041532, filed on Nov. 17, 2017.

(30) Foreign Application Priority Data

Nov. 25, 2016 (JP) .............................. JP2016-229027

(51) Int. Cl.
*A61B 1/00* (2006.01)
*A61B 1/005* (2006.01)
(Continued)

(52) U.S. Cl.
CPC .............. *A61B 1/0016* (2013.01); *A61B 1/00* (2013.01); *A61B 1/00006* (2013.01);
(Continued)

(58) Field of Classification Search
CPC ....................................... A61B 1/00147–0016
See application file for complete search history.

(56) References Cited

U.S. PATENT DOCUMENTS

2008/0262305 A1\* 10/2008 Omoto ............... A61B 1/00006
600/118
2010/0063601 A1\* 3/2010 Sankai ................... B25J 9/0006
623/25

FOREIGN PATENT DOCUMENTS

JP 2013-158569 A 8/2013
JP 2013-158612 A 8/2013
(Continued)

OTHER PUBLICATIONS

International Search Report dated Jan. 30, 2018 issued in PCT/JP2017/041532.
(Continued)

*Primary Examiner* — Alexandra L Newton
(74) *Attorney, Agent, or Firm* — Scully, Scott, Murphy & Presser, P.C.

(57) ABSTRACT

An endoscope apparatus includes an elongated insertion portion, a self-propelling mechanism configured to be rotatably driven to advance and retract the insertion portion, and a motor configured to supply a drive force to the self-propelling mechanism. A control apparatus for the endoscope apparatus includes a current controller configured to supply a motor current to the motor to control driving of the motor, a motor current detector configured to detect a value of the motor current, a motor current change amount detector configured to detect an amount of change in the value of the motor current, and a limit controller configured to stop a supply of the motor current by the current controller according to the amount of change.

4 Claims, 4 Drawing Sheets

(51) Int. Cl.
    *G02B 23/24* (2006.01)
    *A61B 1/05* (2006.01)
(52) U.S. Cl.
    CPC ........ *A61B 1/0051* (2013.01); *A61B 1/00133* (2013.01); *G02B 23/24* (2013.01); *A61B 1/00045* (2013.01); *A61B 1/00156* (2013.01); *A61B 1/05* (2013.01); *G02B 23/2476* (2013.01)

(56) References Cited

FOREIGN PATENT DOCUMENTS

| | | |
|---|---|---|
| JP | 2014-004268 A | 1/2014 |
| WO | WO 2016/009711 A1 | 1/2016 |
| WO | WO 2016/157627 A1 | 10/2016 |

OTHER PUBLICATIONS

English translation of International Preliminary Report on Patentability dated Jun. 6, 2019, together with the Written Opinion received in related International Application No. PCT/JP2017/041532.

\* cited by examiner

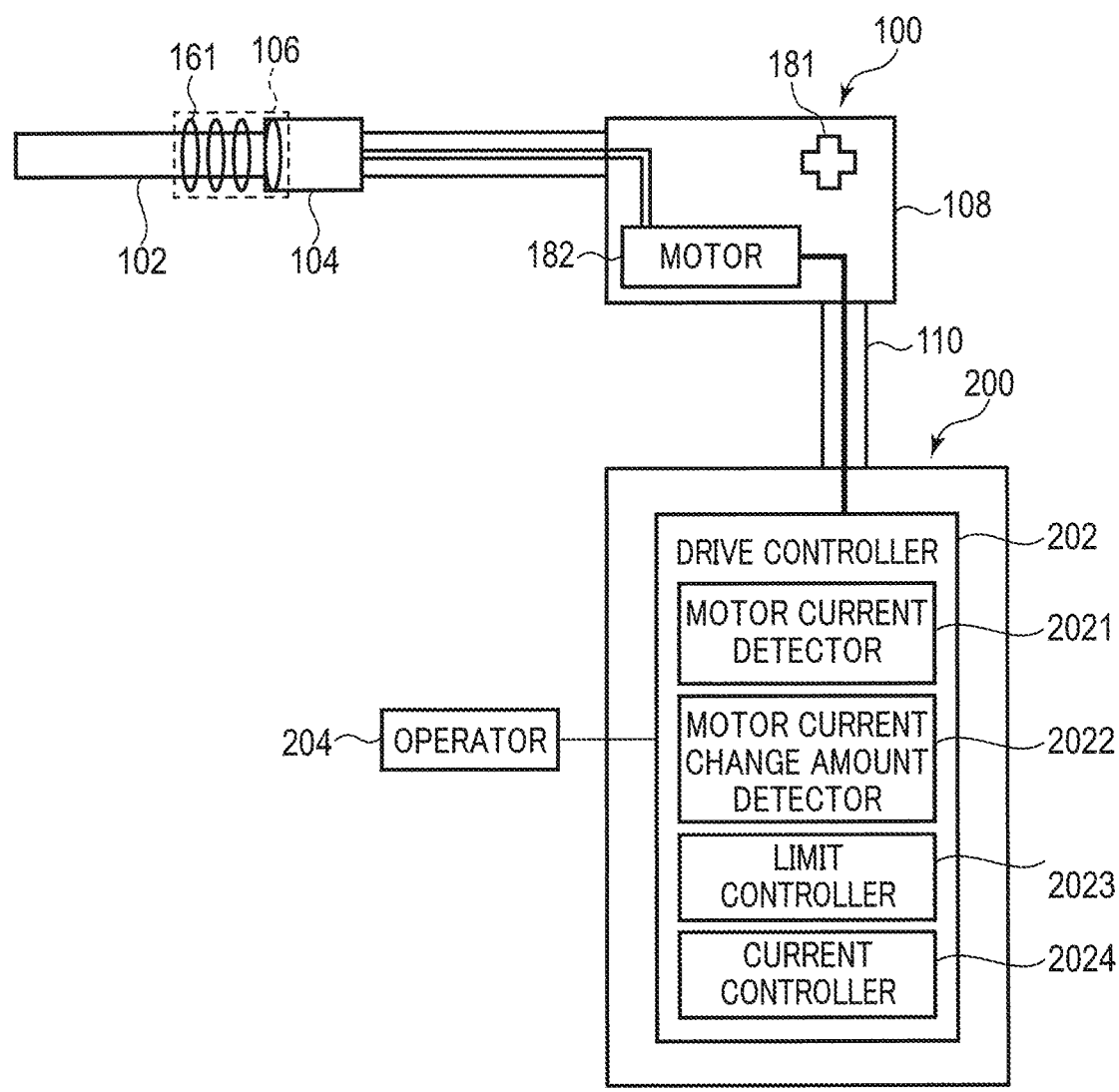
F I G. 1
| INCREASE RATE (MA/S) | TORQUE LIMIT VALUE (MA) |
|---|---|
| 0~20 | 180 |
| 21~40 | 160 |
| 41~ | 140 |
F I G. 2

CONTROL APPARATUS FOR ENDOSCOPE APPARATUS AND ENDOSCOPE APPARATUS

CROSS-REFERENCE TO RELATED APPLICATIONS

This application is a Continuation Application of PCT Application No. PCT/JP2017/041532, filed Nov. 17, 2017 and based upon and claiming the benefit of priority from the prior Japanese Patent Application No. 2016-229027, filed Nov. 25, 2016, the entire contents of both of which are incorporated herein by reference.

FIELD

Exemplary embodiments relate to a control apparatus for an endoscope apparatus and an endoscope apparatus.

BACKGROUND

Known as endoscope apparatuses for insertion into the lumen are self-propelling endoscope apparatuses. Self-propelling endoscope apparatuses advance and retract an insertion portion by propulsive force generated by, for example, rotating a rotating body provided about the insertion portion by a motor. The inserting or retracting operations of the insertion portion of such endoscope apparatuses performed by a user are assisted.

Endoscope apparatuses generally have a torque limit function for stopping rotation when the motor torque (motor current) for the self-propelling becomes equal to or greater than a predetermined torque limit value. For example, Jpn. Pat. Appln. KOKAI Publication No. 2014-004268 suggests an endoscope insertion assisting tool that sets, as a torque limit value, a value obtained by adding a fixed value to a minimum torque value within a predetermined time that is stored in a torque history unit. According to Jpn. Pat. Appln. KOKAI Publication No. 2014-004268, the torque limit value is set in consideration of the internal resistance of the self-propelling mechanism.

SUMMARY

According to an embodiment, there is provided a control apparatus for an endoscope apparatus including an elongated insertion portion, a self-propelling mechanism configured to be rotatably driven to advance and retract the insertion portion, and a motor configured to supply a drive force to the self-propelling mechanism, the control apparatus comprising: a current controller configured to supply a motor current to the motor to control driving of the motor; a motor current detector configured to detect a value of the motor current; a motor current change amount detector configured to detect an amount of change in the value of the motor current; and a limit controller configured to stop a supply of the motor current by the current controller according to the amount of change.

According to an embodiment, there is provided an endoscope apparatus comprising: an elongated insertion portion; a self-propelling mechanism configured to be rotationally driven to advance and retract the insertion portion; a motor configured to supply a drive force to the self-propelling mechanism; a current controller configured to supply a motor current to the motor to control driving of the motor; a motor current detector configured to detect a value of the motor current; a motor current change amount detector configured to detect an amount of change in the value of the motor current; and a limit controller configured to stop a supply of the motor current by the current controller according to the amount of change.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

FIG. 1 is a schematic view showing a configuration of the endoscope apparatus according to an embodiment of the present invention.

FIG. 2 is a view showing an example of a table associating increase rates of the motor current and torque limit values.

DETAILED DESCRIPTION

Figure 3:
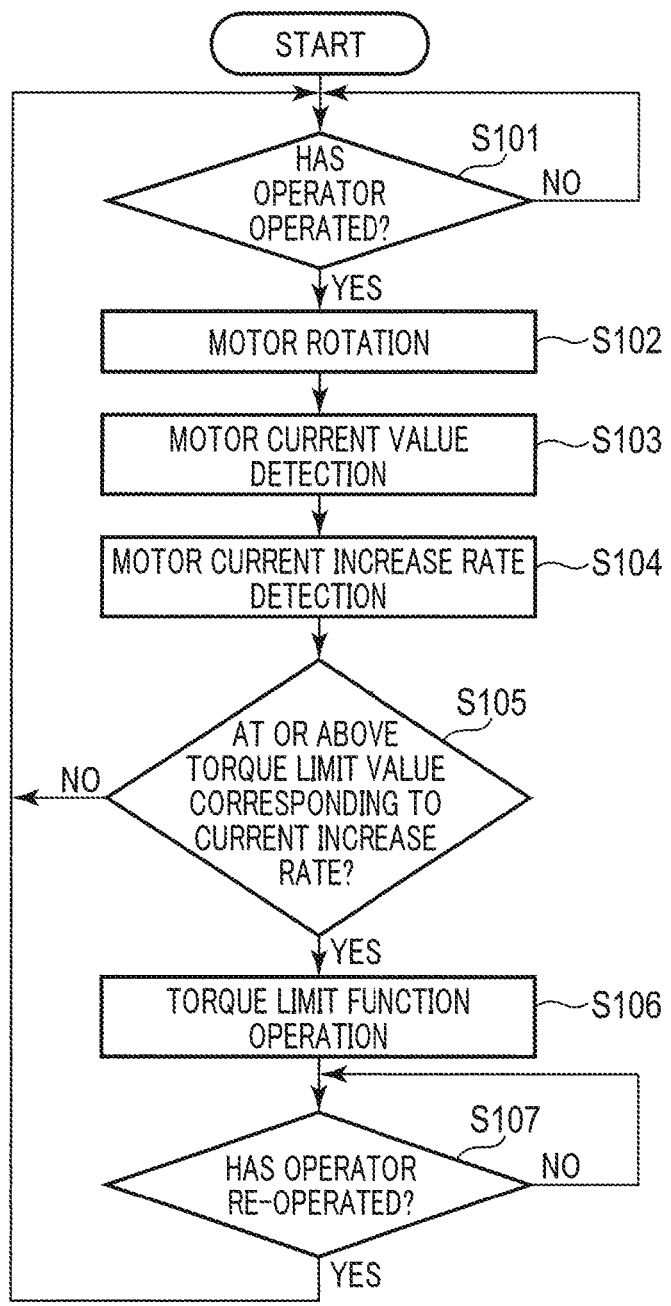
FIG. 3 is a flowchart showing an example of operations of the endoscope apparatus according to the embodiment of the present invention.

Hereinafter, an embodiment of the present invention will be described with reference to the drawings. FIG. 1 is a schematic view showing a configuration of the endoscope apparatus according to an embodiment of the present invention. As shown in the figure, an endoscope apparatus 1 includes an endoscope 100 and a control apparatus 200. It should be noted that the endoscope apparatus 1 in fact includes a light source apparatus for controlling the illumination inside the living body from the endoscope 100, and a monitor for displaying images obtained by the endoscope 100. However, the light source apparatus and the monitor are not shown in FIG. 1.

The endoscope 100 is a rotary self-propelling endoscope with an insertion portion 102. The insertion portion 102 is elongated and configured to be inserted into a living body. The endoscope 100 further includes a control unit 108 for performing various operations of the endoscope 100. The control unit 108 is held by a user. Hereinafter, the side where the distal end of the insertion portion 102 is will be referred to as the distal end side, and the side where the control unit 108 of the insertion portion 102 is provided will be referred to as the proximal end side. The direction from the distal end side to the proximal end side of the insertion portion 102 is defined as the longitudinal direction. The control unit 108 of the endoscope 100 and the control apparatus 200 are connected via a cable 110.

The distal end portion of the insertion portion 102 is configured not to be bent. An image sensor is provided at the distal end portion. The image sensor generates an image signal based on, for example, a subject image on the distal end side of the insertion portion 102. The image signal generated by the image sensor is transmitted to the control apparatus 200 via an image signal line running through the insertion portion 102 and the cable 110.

The proximal end side of the insertion portion 102 includes a portion actively bending according to operations of an operating unit 181 provided in the control unit 108, and a portion passively bending according to external force. Attached to the bending portion of the insertion portion 102 is a rotating unit 104 for transmitting the drive force of a motor 182 that is built into the control unit 108. Attached to the distal end side of the rotating unit 104 is a power spiral tube 106 that is a rotating body. The power spiral tube 106 is tubular-shaped and made from a soft material such as a rubber or resin, and mounted to be rotatable about the longitudinal axis of the bending portion. On the outer peripheral surface of the power spiral tube 106, a spiral fin 161 along the longitudinal axis of the power spiral tube 106 is provided. It should be noted that the power spiral tube 106 may be configured to be detachable from the rotating unit 104.

The motor 182 is connected to the control apparatus 200 via an actuator current signal line running through the control unit 108 and the cable 110. The motor 182 operates by operations using an operator 204. The rotational force of the motor 182 is transmitted to the rotating unit 104. As a result, the fin 161 provided on the power spiral tube 106 rotates about the longitudinal axis.

The fin 161 rotating while being in contact with a wall portion such as the inner wall of the lumen generates a frictional force. The fin 161 contacting, for example, folds in the small intestine and the large intestine present on the inner wall of the small intestine or the large intestine causes frictional force to act onto the insertion portion 102. This frictional force causes the insertion portion 102 to self-propel. As the insertion portion 102 self-propels, the user's insertion operation and retraction operation of the insertion portion 102 are being assisted. It should be noted that when the motor 182 rotates forward, the insertion portion 102 self-propels in the direction of insertion, and that when the motor 182 rotates backward, the insertion portion 102 self-propels in the direction of retraction. The motor 182 comprises a pulse generator. The pulse generator generates a pulse signal (rotation speed signal) corresponding to the rotation speed of the motor 182. The pulse generator inputs the rotation speed signal to the control apparatus 200 via a rotation speed signal line running through the cable 110. The rotational speed signal controls the rotational speed of the motor 182.

The operator 204 is, for example, a foot switch. The foot switch includes a forward pedal and a backward pedal. When the forward pedal is depressed by the user, an instruction signal for rotating the motor 182 forward is output. When the backward pedal is depressed by the user, an instruction signal for rotating the motor 182 backward is output. The forward pedal and the backward pedal are each configured to generate a signal with magnitudes corresponding to the amount of depression. Although in the present scenario, it is assumed that the operator 204 is a foot switch, the operator 204 may be, for example, a switch etc. provided in the control unit 108.

The control apparatus 200 controls each element of the endoscope apparatus 1. The control apparatus 200 comprises at least a drive controller 202. The drive controller 202 is composed of, for example, a CPU and an ASIC, and includes the function of a motor current detector 2021, the function of a motor current change amount detector 2022, the function of a limit controller 2023, and the function of a current controller 2024. Each of these functions of the drive controller 202 may be realized by a single hardware or software, or by a plurality of hardware or software. Some of the functions may also be provided separately from the drive controller 202.

The motor current detector 2021 detects motor current values as drive currents of the motor 182 output from the current controller 2024, and inputs the detected motor current values to the motor current change amount detector 2022.

The motor current change amount detector 2022 detects an amount of variation in the motor current values over a predetermined period (for example, 200 ms). This amount of variation in the motor current values is, for example, the increase rate of the motor current during a set period of time. The increase rate of the motor current is expressed as the motor current delta obtained over the set period of time divided by time.

The limit controller 2023 controls, based on the motor current value change amount detected by the motor current change amount detector 2022, the torque limit function for the motor 182. This torque limit function is a process of stopping the motor 182 by stopping the supply of motor current from the current controller 2024 to the motor 182, and thereby suppressing the rise in torque of the motor 182. In the present embodiment, the limit controller 2023 determines whether or not to cause the torque limit function for the motor 182 to operate by determining whether or not the motor current value is equal to or greater than a torque limit value that is a predetermined current threshold value. The limit controller 2023 further changes the torque limit value according to the increase rate of the motor current. For example, the limit controller 2023 includes a memory for storing a table associating increase rates and torque limit values as shown in FIG. 2, and, by using the torque limit value corresponding to the increase rate of the motor current detected by the motor current change amount detector 2022, the limit controller 2023 determines whether or not the torque limit function should operate. It should be noted that the torque limit value decreases as the increase rate increases, as shown in FIG. 2. If the increase rate of the motor current is large, for example, when the internal load suddenly increases, the torque limit function should really operate. If the torque limit function should really operate, the torque limit value is set small so that the torque limit function can operate easily. Conversely, if the increase rate of the motor current is small, the torque limit function does not instantly need to operate. If the torque limit function does not really need to operate, the torque limit value is set great to make operating the torque limit function difficult. It should be noted that the numerical values and ranges shown in FIG. 2 are merely examples and that they can be changed appropriately.

The current controller 2024 controls the motor current value to be output to the motor 182 by changing the motor voltage by fetching, at predetermined sampling intervals, a rotation speed signal output by the pulse generator of the controller 108, and using the fetched rotation speed signal as a feedback signal to convert the rotation speed of the motor 182 into the rotational speed instructed from the operator 204. When the instruction to cause the torque limit function to operate is received from the limit controller 2023, the current controller 2024 stops the motor current input to the motor 182.

Hereinafter, the operations of the endoscope apparatus 1 according to the embodiment of the present invention will be described. FIG. 3 is a flowchart showing an example of the operations of the endoscope apparatus 1 according to the embodiment. The operations in FIG. 3 are controlled by the drive controller 202 of the control apparatus 200. These operations are started, for example, when the power source of the endoscope apparatus 1 is turned on. It should be noted that a process in parallel with the operations in FIG. 3 is performed by which endoscopic images are displayed onto a monitor based on image signals obtained by the image sensor.

In step S101, the drive controller 202 determines whether or not the operator 204 has operated. If, for example, the operator 204 is the foot switch, it is determined whether or not the forward pedal or the backward pedal has been depressed. As long as it is determined in step S101 that the operator 204 has not operated, the determination in step S101 is repeated. If it is determined in step S101 that the operator 204 has operated, the process continues to step S102.

In step S102, the drive controller 202 controls the drive of the motor 182 using the current controller 2024. That is, the current controller 2024 of the drive controller 202 changes the motor voltage so that the rotation speed of the motor 182 becomes the rotation speed corresponding to the depression amount of the foot switch being the operator 204. Subsequently, the process continues to step S103.

In step S103, the motor current detector 2021 of the drive controller 202 detects the motor current. The motor current is detected at predetermined time intervals.

In step S104, the motor current change amount detector 2022 of the drive controller 202 detects the rate of increase in the motor current detected by the motor current detector 2021 at the predetermined time intervals.

In step S105, the limit controller 2023 of the drive controller 202 determines whether or not the motor current value detected by the motor current detector 2021 is equal to or greater than the torque limit value corresponding to the increase rate detected by the motor current change amount detector 2022. As described above, the table associating the increase rates and torque limit values is stored in advance in the memory of the limit controller 2023. If it is determined in step S105 that the motor current value is not equal to or greater than the torque limit value, the process returns to step S101. If it is determined in step S105 that the motor current value is equal to or greater than the torque limit value, the process proceeds to step S106.

In step S106, the limit controller 2023 of the drive controller 202 instructs the current controller 2024 to cause the torque limit function to operate. In response to the instruction, the current controller 2024 stops the motor 182 by stopping the supply of motor current to the motor 182. It should be noted that the user may be notified according to the operations of the torque limit function that the torque limit function has operated.

In step S107, the drive controller 202 determines whether or not the operator 204 has re-operated. If, for example, the operator 204 is the foot switch, the operator 204 has re-operated if the foot switch is released and then depressed again. As long as it is determined in step S107 that the operator 204 has not re-operated, the determination in step S107 is repeated. If it is determined in step S107 that the operator 204 has re-operated, the process returns to step S101.

As described above, according to the present embodiment, the operations of the torque limit function are controlled according to the torque limit value corresponding to the change amount of the motor current. By adopting, for example, the increase rate of the motor current as the change amount of the motor current, it is possible, for example, to reduce the torque limit value when the torque limit function should really operate, e.g. when a sudden rise occurs in internal load, and to increase the torque limit value otherwise, when the torque limit function does not really need to operate, e.g. when the torque rises due to the bending of the spiral tube portion. In this manner, it is possible to suppress the operations of the torque limit function except if needed. This consequently shortens the inspection time and the like.

[Modification]

Hereinafter, a modification of the present embodiment will be described. In the above embodiment, the increase rate of the motor current has been used as the change amount of the motor current. However, the change amount of the motor current does not have to be the increase rate of the motor current. The below modification is an example using the motor current integrated value during a predetermined period as the change amount of the motor current. It should be noted that the basic configuration of the endoscope apparatus of the present modification is the same as the configuration described with reference to FIG. 1. In this modification, the motor current change amount detector 2022 detects the motor current integrated value over a predetermined period of time as the change amount of the motor current value.

Figure 4:
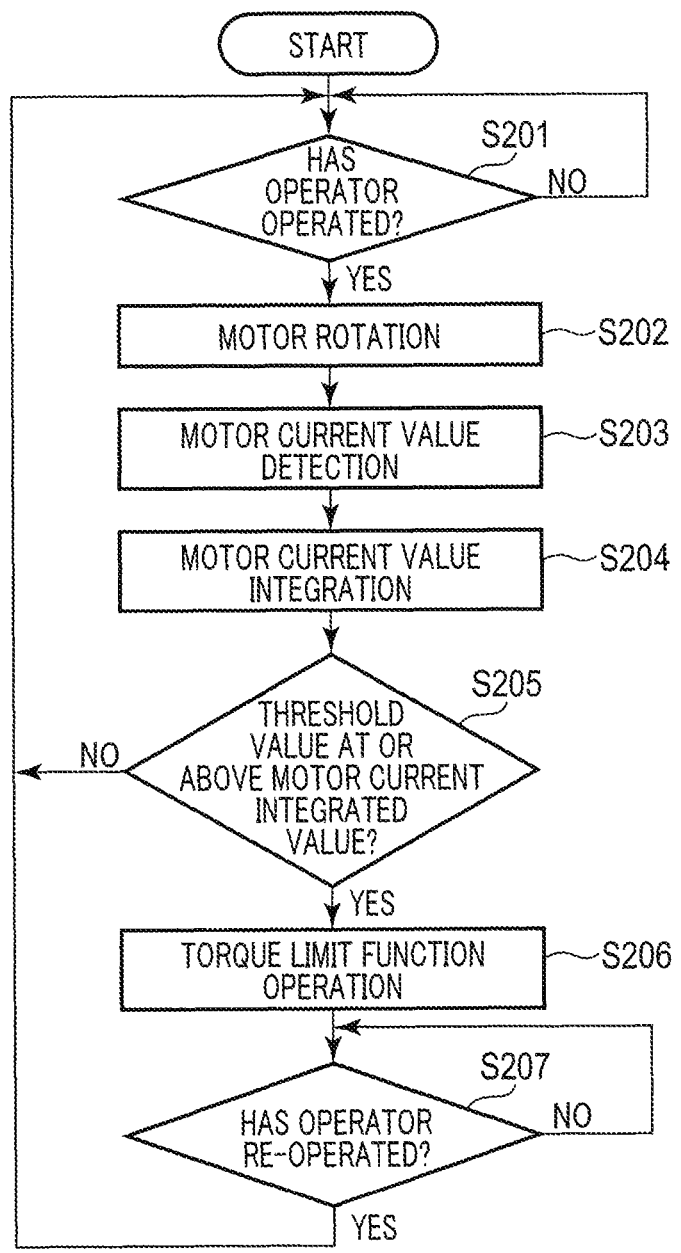
FIG. 4 is a flowchart showing an example of operations of the endoscope apparatus according to a modification.

Hereinafter, the operations of the endoscope apparatus 1 according to the modification will be described. FIG. 4 is a flowchart showing an example of the operations of the endoscope apparatus 1 according to the modification. It should be noted that description of those processes similar to those in FIG. 3 will be omitted as appropriate.

In step S201, the drive controller 202 determines whether or not the operator 204 has operated. As long as it is determined in step S201 that the operator 204 has not operated, the determination in step S201 is repeated. When it is determined in step S201 that the operator 204 has operated, the process proceeds to step S202.

In step S202, the drive controller 202 controls the drive of the motor 182 using the current controller 2024.

In step S203, the motor current detector 2021 of the drive controller 202 detects the motor current. The motor current detector 2021 detects the motor current at, for example, predetermined time intervals (25 ms).

Figure 5:
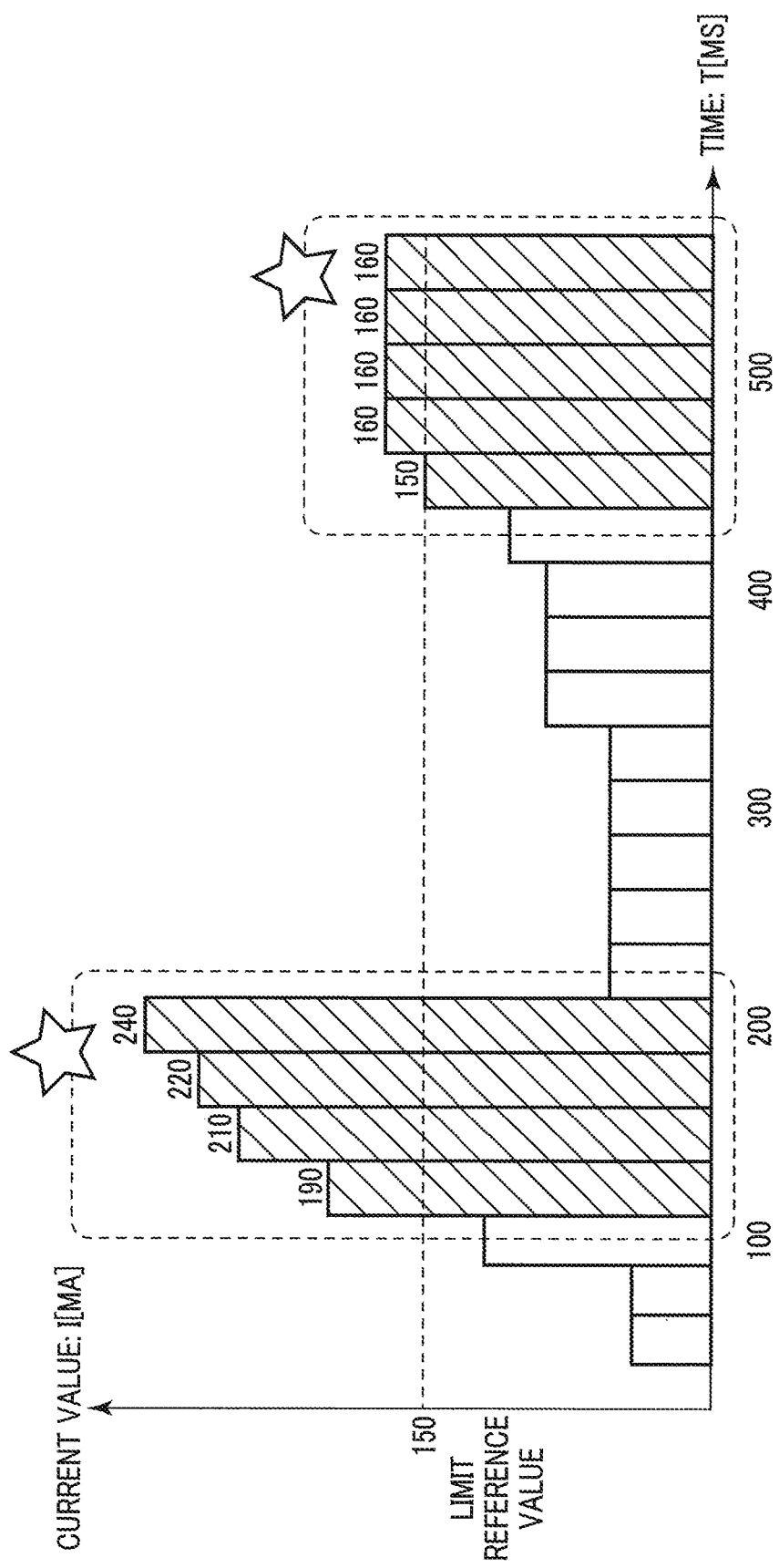
FIG. 5 is a view explaining the operations of the modification.

In step S204, the motor current change amount detector 2022 of the drive controller 202 detects the motor current integrated value in the motor current detector 2021. The motor current integrated value is, for example, the integrated value since the point in time at which the predetermined limit reference value is reached or exceeded. For example, in the example of FIG. 5, the limit reference value is 150 mA. In this case, as shown by the dashed line boxes in FIG. 5, the detection of the integrated value is started when the motor current value reaches 150 mA or more, and when the motor current value falls below the limit reference value, the detection of the integrated value is terminated. At this point, the integrated value is reset.

In step S205, the limit controller 2023 of the drive controller 202 determines whether or not the value of the integrated value is equal to or greater than the predetermined threshold value (for example, 800 mA). It should be noted that this threshold value is stored in advance in the memory of the limit controller 2023. If it is determined in step S205 that the integrated value is not equal to or greater than the threshold value, the process returns to step S201. If it is determined in step S205 that the integrated value is equal to or greater than the threshold value, the process proceeds to step S206. Since the operations of the torque limit function are determined by the integrated value, the time until the torque limit function operates decreases if a motor current flows which is much greater than the limit reference value (see first integrated part in FIG. 5), and conversely, the time until the torque limit function operates increases if a motor current flows which is close to the limit reference value (see second integrated part in FIG. 5).

In step S206, the limit controller 2023 of the drive controller 202 instructs the current controller 2024 to cause the torque limit function to operate. In response to the instruction, the current controller 2024 stops the motor 182 by stopping the supply of motor current to the motor 182. It should be noted that the user may be notified according to the operations of the torque limit function that the torque limit function has operated.

In step S207, the drive controller 202 determines whether or not the operator 204 has re-operated. As long as it is determined in step S207 that the operator 204 has not re-operated, the determination in step S207 is repeated. If it is determined in step S207 that the operator 204 has re-operated, the process returns to step S201.

As described above, according to the present modification, the operation of the torque limit function is controlled in accordance with the torque limit value corresponding to the change amount of the motor current as in the embodiment. By adopting, for example, the motor current integrated value as the change amount of the motor current, it is possible to set the time at which the torque limit function should really operate, e.g. when a sudden rise in the internal load occurs, similar to the case in which the increase rate is adopted.

According to the present modification, it is determined, based on the integrated value, whether or not the torque limit function should operate. Although the motor current value suddenly rises even when, for example, starting the motor, the instantaneous change in motor current can be ignored by determining, based on the integrated value, whether or not the torque limit function should operate. In this manner, the likelihood of making erroneous determinations on the operations of the torque limit function can be reduced.

It should be noted that although in the present modification the integrated value is directly compared with the threshold value, the integrated value and the torque limit value may be associated as in the embodiment, and whether or not the torque limit function should operate may be determined by comparing the torque limit value corresponding to the integrated value with the motor current value. When associating the integrated value with the torque limit value, the torque limit value is set small if the motor current integrated value is large, and the torque limit value is set large if the motor current integrated value is small. Further, although in the modification, the motor current integrated value exceeding the reference value is compared with the threshold value, the integrated value that includes the motor current not exceeding the reference value may be compared with the threshold value.

Although the present invention has been described based on the above embodiment, the present invention is not limited to the above embodiment, meaning that various modifications and applications within the scope of the gist of the present invention are obviously possible. For example, in the above embodiment, the rotating body for advancing and retracting the insertion portion 102 of the endoscope 100 is the power spiral tube 106, but in contrast to this, the art of the present embodiment is applicable to various insertion devices that advance and retract the insertion portion 102 by the rotating body.

Each of the processes of the above embodiment can be stored as a program executable by the drive controller 202 that is a computer. Each of the processes can also be stored in a storage medium of an external storage device such as a magnetic disk, an optical disk, a semiconductor memory, and which can then be distributed. The drive controller 202 can read the program stored in the storage medium of the external storage device, so that the operations can be controlled using the read program to execute the above processes.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control apparatus for an endoscope apparatus including an elongated insertion portion, a self-propelling mechanism configured to be rotatably driven to advance and retract the insertion portion, and a motor configured to supply a drive force to the self-propelling mechanism, the control apparatus comprising:
a controller configured to:
supply a motor current to the motor to control driving of the motor;
detect a value of the motor current;
detect an integrated value of the motor current over a predetermined fixed period of time that is less than a life of the motor as an amount of change; and
stop operations of the motor when the integrated value is equal to or greater than a predetermined value.

2. The control apparatus according to claim 1, wherein the controller is configured to detect an integrated value of the motor current equal to or greater than a predetermined limit reference value over the predetermined period of time as the amount of change.

3. The control apparatus according to claim 1, wherein
the controller is configured to stop the supply of the motor current to the motor when the motor current reaches or exceeds a predetermined torque limit value, and
set the torque limit value to decrease according to an increase of the integrated value.

4. An endoscope apparatus comprising:
an elongated insertion portion;
a self-propelling mechanism configured to be rotationally driven to advance and retract the insertion portion;
a motor configured to supply a drive force to the self-propelling mechanism;
a controller configured to:
supply a motor current to the motor to control driving of the motor;
detect a value of the motor current;
configured to detect-an integrated value of the motor current over a predetermined fixed period of time that is less than a life of the motor as an amount of change; and
stop operations of the motor when the integrated value is equal to or greater than a predetermined value.

* * * * *